United States Patent
Lang et al.

(10) Patent No.: US 9,816,866 B2
(45) Date of Patent: Nov. 14, 2017

(54) METHOD FOR EXAMINATION OF A SAMPLE BY MEANS OF THE HEAT FLOW THERMOGRAPHY

(71) Applicant: FEI EFA, Inc., Fremont, CA (US)

(72) Inventors: Haymo Lang, Igensdorf (DE); Jochen Mielke, Rutesheim (DE)

(73) Assignee: FEI EFA, Inc., Fremont, CA (US)

( * ) Notice: Subject to any disclaimer, the term of this patent is extended or adjusted under 35 U.S.C. 154(b) by 631 days.

(21) Appl. No.: 14/362,122

(22) PCT Filed: Dec. 10, 2012

(86) PCT No.: PCT/EP2012/074982
§ 371 (c)(1),
(2) Date: May 31, 2014

(87) PCT Pub. No.: WO2013/083846
PCT Pub. Date: Jun. 13, 2013

(65) Prior Publication Data
US 2014/0328370 A1   Nov. 6, 2014

(30) Foreign Application Priority Data
Dec. 10, 2011 (DE) .................. 10 2011 120 808

(51) Int. Cl.
*G01J 5/00* (2006.01)
*G01J 5/32* (2006.01)
*G01N 25/72* (2006.01)

(52) U.S. Cl.
CPC ............... *G01J 5/32* (2013.01); *G01N 25/72* (2013.01); *G01J 2005/0077* (2013.01); *G01J 2005/0081* (2013.01)

(58) Field of Classification Search
CPC .................... G01J 5/32; G01J 25/72
(Continued)

(56) References Cited

U.S. PATENT DOCUMENTS

| 7,554,086 B2 | 6/2009 | Shepard et al. |
| 2002/0172410 A1 | 11/2002 | Shepard |

(Continued)

FOREIGN PATENT DOCUMENTS

| DE | 10150633 A1 | 4/2003 |
| DE | 102006043339 B4 | 11/2010 |
| EP | 1852697 A1 | 11/2007 |
| EP | 1203224 B1 | 7/2008 |
| JP | 2004-69439 A | 3/2004 |
| RU | 2343465 C1 | 1/2009 |

OTHER PUBLICATIONS

International Search Report for PCT/EP2012/074982 dated Apr. 8, 2013.
(Continued)

*Primary Examiner* — David Porta
*Assistant Examiner* — Meenakshi Sahu
(74) *Attorney, Agent, or Firm* — Klarquist Sparkman, LLP

(57) ABSTRACT

The invention provides a method for a non-destructive, non-contacting and image forming examination of a sample by means of the heat flow thermography method where the examination consists of evaluating an existence and/or depth distance values of any heat flow velocity transitions below a surface of the sample, wherein the sample is excited by heat pulses of at least one excitation source, and a thermal flow originating therefrom is captured by at least one infrared sensor in an image sequence of thermal images, and wherein the thermal images obtained from the image sequence are evaluated by means of a signal and image processing and depicting a thermal flow with a resolution in time and in space. The method comprises: exciting the sample at least twice independently from each other by means of the heat pulses from the excitation source where a second excitation and any succeeding excitation is delayed with respect to a preceding excitation by a time delay whereby the start of the captured sequence happens at (Continued)

Figure 1:
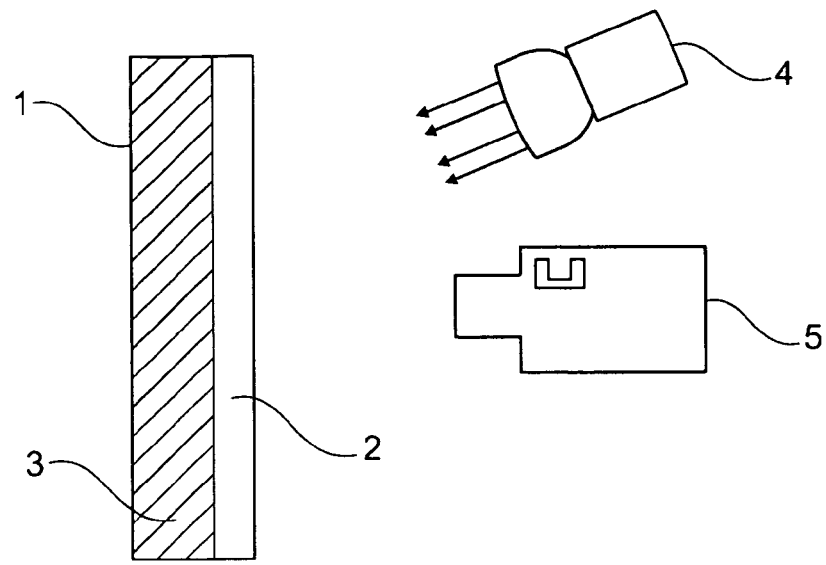

another defined point of time within the time between two images within an image sequence; detecting the respective total thermal flow processes generated by the at least two excitation processes of the sample by the infrared sensor in the independent image sequences containing the excitation as well as the thermal answer signal from the sample, combining all captured image sequences to a total image sequence in which all images are arranged in a sequence which is correct in time with respect to the point of time of the pulse like excitation, and extracting from the total image sequence, in a manner known per se, an indication of the depth distance of a heat flow velocity transition from a surface of the sample. Therein, the heat flow velocity transitions can be a boarder layer of a layered material or defects in a substrate or below a surface of a work piece.

16 Claims, 3 Drawing Sheets

(58) Field of Classification Search
USPC .................................. 250/338.1, 341.4, 342
See application file for complete search history.

(56) References Cited

U.S. PATENT DOCUMENTS

| 2003/0137318 | A1 | 7/2003 | Enachescu et al. |
| 2005/0008215 | A1* | 1/2005 | Shepard ................ G01N 25/72 |
| | | | 382/141 |
| 2005/0056786 | A1 | 3/2005 | Shepard et al. |

OTHER PUBLICATIONS

International Preliminary Report on Patentability for PCT/EP2012/074982 dated Jun. 19, 2014.
Carslaw, H. S., et al., "Conduction of Heat in Solids", 2nd Edition, Oxford University Press, 1959, pp. 297-326.
Database WPI—Week 200427 Thomson Scientific, London, GB; AN 2004-287592, XP002694400.
Maldague, Xavier P.V., "Theory and Practice of Infrared Technology for Non-destructive Testing", John Wiles & Sons, Inc., Apr. 2001, pp. 527-536.

* cited by examiner

METHOD FOR EXAMINATION OF A SAMPLE BY MEANS OF THE HEAT FLOW THERMOGRAPHY

RELATED APPLICATIONS

The present application is the national phase of International Application No. PCT/EP2012/074982, filed on Dec. 10, 2012, which claims the benefit of priority to German Patent Application No. 102011120808.2, filed on Dec. 10, 2011, and the disclosures of which are hereby incorporated herein by reference in their entireties.

The invention relates to a method for a non-destructive, non-contacting and image forming examination of a sample by means of the heat flow thermography method where the examination consists of evaluating an existence and/or depth distance values of any heat flow velocity transitions below a surface of the sample, wherein the sample is excited by heat pulses of at least one excitation source, and a thermal flow originating therefrom is captured by at least one infrared sensor in an image sequence, and wherein thermal images obtained from the image sequence are evaluated by means of a signal and image processing and depicting a thermal flow with a resolution in time and in space, A non-destructive and non-contacting measurement of physical thermal characteristics of a layered material can for example be carried out with the aid of a punctual laser excitation as well as a plurality of punctual detectors (RU 2343465 C1). Therein, the laser beam as well as the detectors are to be moved along the surface of the material to be inspected in order to ensure a surface covering measurement. This method is, however, also not adapted to keep pace with an industrial fabrication.

Besides the known nondestructive methods for evaluating the layer structure of a layered material, as for example methods using ultra sound, a magnetic field and an eddy current, the active heat flow thermography has been established in the last years for a imaging measurement method. The procedures implemented with this method are based on the evaluation of the heat transport through the material to be measured as a function of the surface temperature in transmission or reflection. The generated heat flow is excited by single energy pulses or by periodically repeating energy pulses and is than captured by means of an infrared sensor in a sequence of images. From the analysis of the pixel related transitions, a characteristic value is extracted (for example by a Fourier transformation or lock-in-correlation) which describes the behavior in time of the heat wave through the layer system and which is correlated to a layer thickness value evaluated by other, destructive or contacting methods ("Theory and Practice of Infrared 5 Technology for Non-destructive Testing", Xavier P. V. Maldague, John Wiles & Sons, Inc., 2001). As a pulse like excitation in such a method, a flash (EP 1 203 224 B1) or a short application of a heating or cooling gas, respectively, can be used (DE 10 2006 043 339 B4).

The heat flow thermography has been established in the past years as a non-contacting and nondestructive examination method. According to this method, a sample is excited by at least one source in order to generate a heat flow. The heat radiation immediate from the sample is captured by at least one infrared sensor in a sequence of images, and is passed on to a calculating unit. Resulting images of various types can be generated in the computing unit whereby a thermal image or an amplitude- or phase image, respectively is retrieved (Theory and Practice of Infrared Technology for Nondestructive Testing, Xavier P. V. Maldague—John Wiley & Sons, Incl., 2001).

The method for examining a joint connection by thermography is described in DE 10 2001 120 808.2 wherein an imaging, time and local high resolution is provided which is scalable in both parameters examination of a joint connection (for example resistance weld point or laser weld seam) out of such thermally thin layers. Thereby, for example a weld lens in a resistance weld point to be examined can be differentiated from its near surroundings (welding adhesive). In this context, intensity variations of the excitation source, the state and the characteristics of the material surface as well as the thickness of the material are not supposed to influence substantially the measurement result. Therefore, a resulting image is to be used which does not represent an absolute value of the heat flow or its velocity, respectively, through the weld connection to be examined, but rather a corresponding local velocity difference of the heat flow. Such a resultant image can for example be generated by the infrared lock-in thermography wherein a so-called phase image is generated (Theory and Practice of Infrared Technology for Nondestructive Testing, Xavier P. V. Maldague, John Wiley & Sons, Inc., 2001). Such a phase image shows the run time of thermal waves in the material assembly. Thereby, the heat conductivity differences between different image points of the material connection to be examined become visible.

The geometrical resolution of a measurement system may be extended, therein, by means of high resolution cameras and respective objective lenses, respectively, almost arbitrarily. The maximum time resolution is, however, fixedly defined by the camera system. The image repetition rates achievable by modern detector matrices when using all presently available decoder elements (full image mode) are in the range of 100-200 images per second. This is not sufficient in order to resolve the thermal answer signals of thinner layers or of layers out of thermally fast materials which form the so-called thermally thin layers.

At present, this is attempted to be achieved by a large restriction of the sensitive detector surface (partial-image-mode), for example 16×16 pixel, which, however, has the consequence of the loss of the geometrical resolution and, in spite of that, cannot ensure a sufficient resolution in time. The modern layered material consists mostly out of such so-called thermally thin layers. Therefore, the examination of the total layer structure of a layered material with high time and local resolution is of exceptional economical and technical importance.

Starting from this, it is the object of the invention to provide a method for a non-destructive, non-contacting and image forming examination of a sample by means of the heat flow thermography method where the examination consists of evaluation a depth distance values of any heat flow velocity transitions from a surface of the sample with high time and local resolution wherein the thermal material parameters may flexibly, quickly and robustly be reconstructed/examined under industrial conditions.

For this purpose, the method of the invention comprises exciting the sample at least twice independently from each other by means of the heat pulses from the excitation source where a second excitation and any succeeding excitation is delayed with respect to preceding excitation by a time delay whereby the start of the captured sequence happens at another defined point of time within the time between two images within an image sequence; detecting the respective total thermal flow processes generated by the at least two excitation processes of the sample by the infrared sensor in the independent image sequences containing the excitation procedure as well as the thermal answer signal from the sample, combining all captured image sequences to a total image sequence in which all images are arranged in a sequence which is correct in time with respect to the point of time of the pulse like excitation, and extracting from the total image sequence, in a manner known per se, an indication of the depth distance of a heat flow velocity transition from a surface of the sample.

According to a specific embodiment of the invention the sample is excited by means of at least one pulse like excitation source. The excitation happens at least twice independently from each other. The respective total heat flow processes of the layered material are detected by at least one infrared sensor in independent image sequences. Each image sequence contains, therein, the excitation procedure as well as the thermal answer signal of each layer to be evaluated of the layered material up to the point of time of the thermal equilibrium. Furthermore, each image sequence is captured with a delay $\Delta t$ with respect to the point in time of the pulse like excitation so that the start of the each captured picture sequence is at another defined point of time within the time to between two images within an image sequence. Thereby, an in principal arbitrary, time wise scanning of a function of the intensity of the examined surface in transmission or reflection is ensured. Thereafter, all captured image sequences are combined to a total image sequence within which all images are arranged in a sequence which is correct in time with respect to the point of time of the pulse like excitation. This may be, for example, achieved thereby that the pixel related intensity curves from the total image sequence are accordingly smoothened. Subsequently, the total image sequence is used for reconstructing at least one layer of the total layer structure of the layered material. For this purpose, the parameters are extracted pixel related from the respective heat flow processes of the total image sequence with an increased local (complete-image-mode) and time wise resolution. The respective layer thickness values d calculated therefrom are then combined to an image covering the total area.

According to a preferred embodiment of the method of the invention the indication of the depth distance of a heat flow velocity transition from a surface of the sample comprises the run time parameters $\tau$ related to the surface areas of the sample in a pixel related manner which parameters are an advantageous starting point for the evaluation of the location of the defects.

According to a further preferred embodiment of the method of the invention the total image sequence is corrected such that the pixel related intensity curves comprise a strictly monotones behavior in the areas to be evaluated. This total image sequence is corrected so that the pixel related intensity curves of the total image sequence comprises a strictly monotonous behavior in the areas to be examined, and, thereby, may be processed mathematically in an unambiguous way.

According to a further preferred embodiment of the method of the invention any image sequence extends up the point of time when an equilibrium condition is reached with respect to the dissipation of the heat applied during the excitation of the sample to cover the complete heat flow process.

According to a further preferred embodiment of the method of the invention a periodic excitation of the layered material is used wherein the starting point of the imaging of the respective independent image sequence is displaced with respect to the starting point of the periodic excitation to another defined point in time. Therein, the starting point of imaging of the respective independent image sequences is displaced with respect to the starting point of the periodical excitation. Thereby, a high resolution analysis in space and in time of the pixel related intensity curves is made possible by means of the lock-in-correlation from which the characteristic values are extracted which describe the behavior in time of the heat waves through the layer system.

According to a further preferred embodiment of the method of the invention the delay of the independent image sequences is carried out in equal time portions. According to a preferred embodiment of the invention, the delay $\Delta t$ of the independent image sequences is in equal time portions. This allows a uniform building up of the total image sequence which is used for reconstructing at least one layer of the total layer structure of the layered material.

According to a further preferred embodiment of the method of the invention the length of the equal portions in time of the delay $\Delta t$ of the independent image sequences is defined as the quotient of the time $t_0$ between two images within an image sequence divided by the number of the independently captured image sequences n. Thereby, the increase of the resolution in time of the examination is coupled proportionally to the number of the captured image sequences.

According to a further preferred embodiment of the method of the invention the image intensity of each captured image sequence is corrected so that all captured image sequences have the same intensity offset. This ensures that the intensity values which are derived locally from the same positions but are from different image sequences are combined to respective pixel related intensity curves which have a strictly monotonous behavior in the areas to be evaluated and can, therefore, be processed mathematically unambiguously.

According to a further preferred embodiment of the method of the invention one of the captured image sequence is used as a reference sequence for correcting the image intensity in the rest of the captured image sequences. Thereby, the same intensity of said is ensured for all captured image sequences.

According to a further preferred embodiment of the method of the invention the first captured image sequence serves as a reference sequence for correcting the image intensity in the rest of the captured image sequences. Thereby, the rest of the image sequences can be already used with a correction for the further processing.

According to another aspect of the method of the invention the sample comprises a layered material comprising a base layer and at least one layer additional layer, wherein the run time parameter is extracted related to pixels from the respective thermal flow procedures of the total image sequence, and from the run time parameter respective depth distance values of a heat flow velocity transition from a surface of the layered structure are calculated which are put together to an image covering the surface area of the layered structure of the sample.

The application of the method of the invention to a structure of layered material is only one of many possible applications of the method of the invention. In case of a structure of layered material, the interface between one of the at least two layers and the adjacent layer forms a heat flow velocity transition between the heat flow velocity in one of the layers and the heat flow velocity in the other layer. Since there are two layers, the heat flow velocity by definition is different in the two layers. Therefore, the depth distance of this heat flow velocity transition can be determined by analyzing the thermal images taken during the cause of the excitation and the dissipation of the heat input into the sample.

According to a further preferred embodiment of the method of the invention the reconstruction of at least one layer of the total layer structure of a layered material is carried out based on the physical model thereof wherein the run time parameters of the respective pixel related heat flow processes of the total image sequence are extracted by correlating the respective thermal answer signals of the layered material with the previously calculated pulse answer signals for different run times of appropriate lengths, and wherein all layer thickness values are calculated from the detected run time parameters in knowledge of diffusivity values of corresponding layers of the layered structure. This advantageous embodiment of the method of the invention comprises a time saving and exact method how to evaluate the depth distance of the border surface or interface between the at least two layers of the layered structure.

According to a further preferred embodiment of the method of the invention the reconstruction of one layer of the total layer structure of a layered material, i.e. the reconstruction of the interface between the layer and the underlying layer, is carried out based on the physical model thereof wherein the run time parameters of the respective pixel related heat flow processes of the total image sequence are extracted by correlating the respective thermal answer signals of the layered material with the previously calculated pulse answer signals for different run times of appropriate lengths, and wherein all layer thickness values are calculated from the detected run time parameters in knowledge of diffusivity values of corresponding layers of the layered structure. Therein, the pulse answers $h(\tau)$ of the various run times $\tau$ of appropriate length are calculated beforehand. Thereafter, these are equalized with the respective thermal answer signals of the layered material so that the optimal run time parameter $\tau$ of at least one layer of the layered material can be extracted out of the respective pixel related heat flow processes of the total image sequence. In this way, a fast, flexible and precise calculation of the run time parameter $\tau$ is ensured. Thereafter, the respective layer thickness values d are calculated from the evaluated run time parameter $\tau$ by using a previous knowledge of the diffusivity value $\alpha$ of these layers. Thereby, a very extensive or even impossible definition of the so-called calibration normal can be omitted for calculating the evaluated parameter of the desired layer thickness values d. Thereby, a calibration free and quantitative reconstruction of at least one layer of the total layer structure of the layered material is ensured.

In particular, the invention relates to a non-destructive, non-contacting and imaging measurement method of a total layer structure of a layered material. Thereby, the parameters like the run time $\tau$ as well as the characteristics, for example the thickness d or the diffusivity a of individual layers of the layered material can be measured or controlled, respectively, as well as various interior defects in the material can be evaluated in the course of the industrial sequences production.

According to another aspect of the method of the invention the sample comprises a substrate or a work piece including defects close to a surface of the substrate which defects are heat flow velocity transitions experienced by the heat flow from the surface of the sample into a body of the sample, wherein the indication of presence and depth distance of a particular defect is a hot spot in a respective image of the image sequence which respective image was taken at a time distance from the excitation of the sample related to the depth distance of the defect from the surface of the sample.

As is apparent from the above specification, the method of the invention is applicable in cases where a heat flow velocity transition in a sample or substrate is to be detected where the changes in time of the heat flow dissipation curve or the intensity curve of the thermography curve varies so fast that a full range camera, for example a camera having 640×514 pixel full frame, can not record the changes in the intensity in the image of the heat flow. In other words the method of the invention is applicable in cases where the speed of the camera, i.e. the number of frames that can be taken per second, is to slow to capture the changes of the intensity in the image of the heat flow. For example a camera having 640×514 pixel full frame has a speed of 200 frames per second whereas a frame rate of 2000 frames per second is desired in the case of the examination of layered structures or substrates having defects next to their surface. In such cases, the two or more image sequences can be interleaved in order to improve the time resolution of the recording of the heat flow accordingly.

Embodiments of the invention as well as further features, applications and advantages are explained with reference to the Figures.

FIG. 1 schematically shows a device for capturing the respective total heat flow processes in reflection of a layered material formed by an upper layer on a base layer as one application example of the invention.

Figure 2:
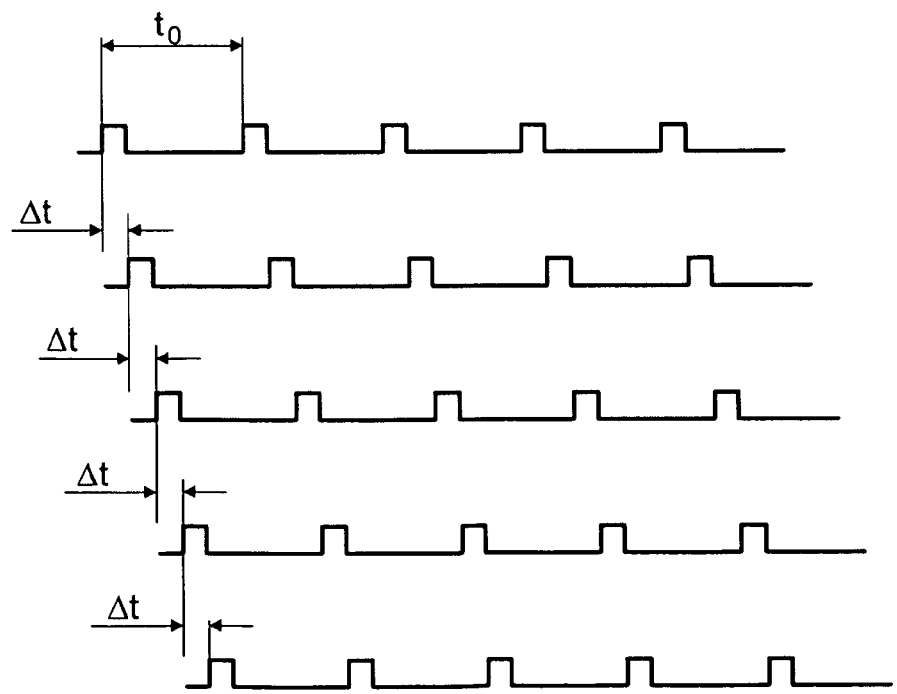

FIG. 2 schematically shows the timing of the capturing of five image sequences which have a delay of $\Delta t$ each to the previous image sequence.

Figure 3:
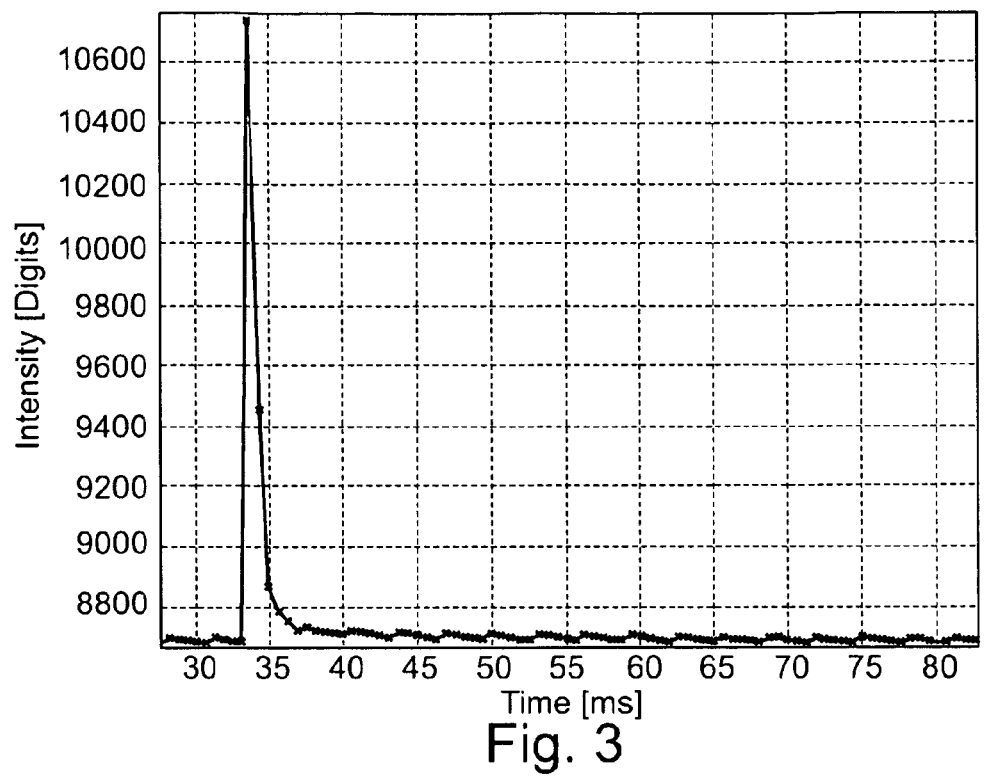

FIG. 3 schematically shows a curve which represents the intensity values of an image point which are from five image sequences and are not yet corrected.

Figure 4:
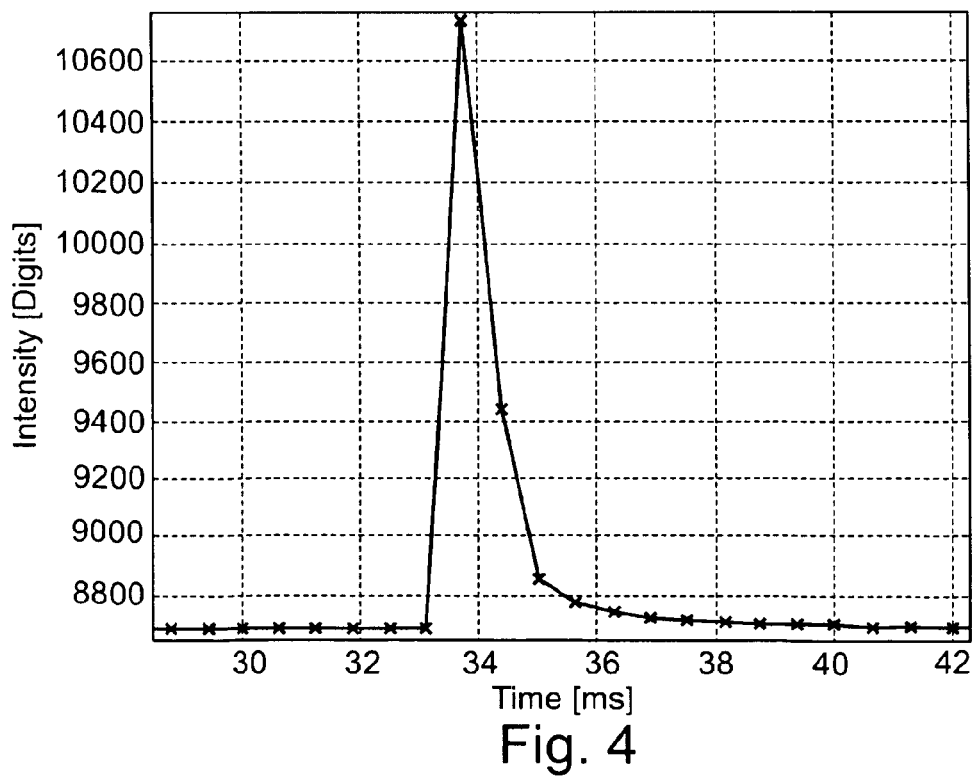

FIG. 4 schematically shows a curve representing the corrected intensity values of an image point which stems from five image sequences.

Figure 5:
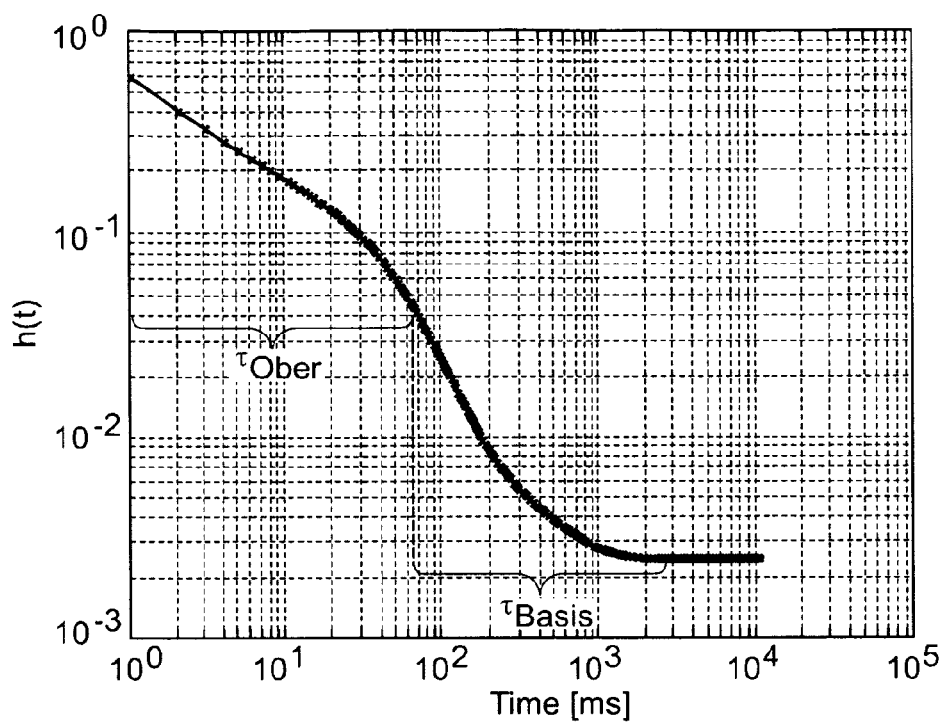

FIG. 5 shows a characteristic curve out of the corrected total sequence of an image point for evaluating the run time parameter t of a two layer material.

Figure 6:
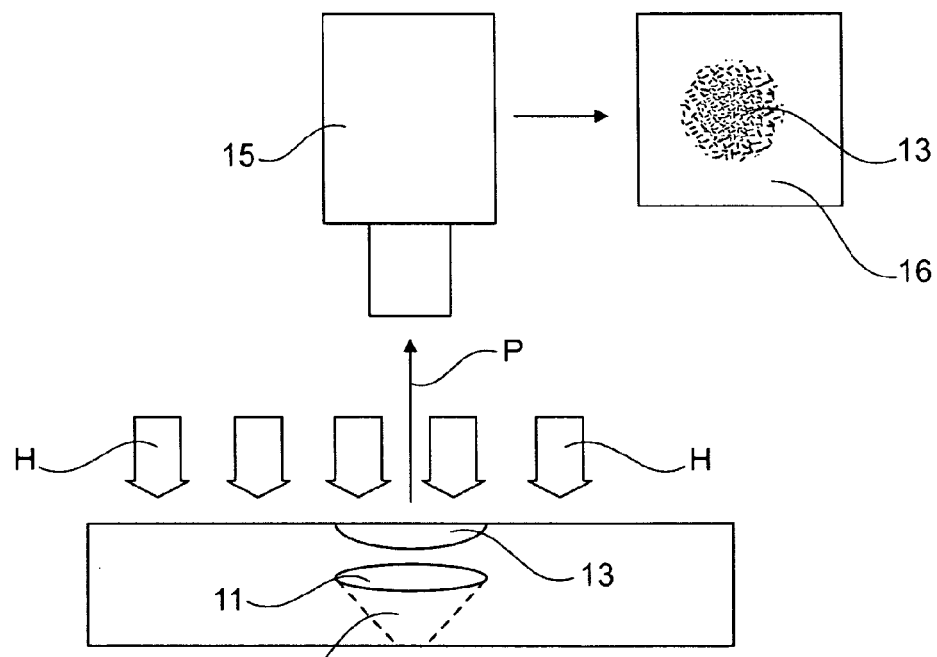

FIG. 6 schematically shows a device for capturing the respective total heat flow processes in reflection of a substrate having defects as another application example of the method of the invention.

FIRST APPLICATION EXAMPLE

In a first example, a material 1 which is formed out of two layers so that an upper layer 2 is located on a base layer 3 (FIG. 1A). The material 1 is examined by means of a thermography system. A flash is used as an excitation source 4 with which the material 1 to be examined is excited fivefold. Upon each pulse like excitation, an independent image sequence is captured by the infrared sensor 5 in reflection (FIG. 2) in which the respective pixel related total heat flow process of the layered material 1 are captured. Each image sequence is captured with a delay of $\Delta t$ with respect to the point in time of the pulse like excitation so that the starting point of the first image sequence is immediately after the excitation, the second image sequence is captured with a delay $\Delta t$ of one fifth of the time $t_0$ between two images within an image sequence and the third image sequence is captured with a delay of $\Delta t$ of two fifth of the time $t_0$ and so on. Within each image sequences, all images are sorted in a correct sequence in time with respect to the point of time of the pulse like excitation. Therein, each image sequence contains the excitation process as well as the thermal answer signal of each layer to be examined of the layered material 1 up to the point of time of the thermal equilibrium.

As long as the respective intensity values of the captured image sequences are not corrected (FIG. 3) they show an increased resolution in time of the evaluated pixel related functions of the surface intensity, but they form pixel related intensity curves of the total sequence which do not comprise a strictly monotonous behavior in the areas to be evaluated. Therefore, they cannot be processed mathematically in an unambiguous way. After this correction the first image sequence serves as a reference sequence in this example, all captured image sequences are subject to the same intensity offset. Therefore, all respective combined pixel related intensity curves in the areas to be evaluated (after the excitation) are strictly monotonous (FIG. 4).

The total image sequences are used now for the reconstruction of the total layer structure of the layered material 1 starting from the physical model thereof as well as from the known excitation signal of the excitation source 4. For this purpose, pulse answers $h(\tau)$ of the total system for different run times t of appropriate length are calculated beforehand from the physical model of the material 1 to be examined, for example by means of the inverse Laplas transformation ("Conduction of Heat in Solids, $2^{nd}$ Edition, Carslaw H. S. and Jaeger J. C., Clearendon Press Oxford, 1959, pages 297 to 326). Therefrom, the respective thermal answer signals of the layered material 1 are equalized mathematically for example with the method of the least squares (Taschenbuch der Mathematik, I. N. Bronstein, K. A. Semendjajew., $25^{th}$ edition, B. G. Teubner Verlagsgesellschaft, Stuttgart, Leipzig and Verlag Nauka, Moskau, 1991). Thereby, the optimal run time parameters $\tau_{upper}$ and $\tau_{base}$ can be extracted out of the respective areas of the intensity curves of the total image sequence (FIG. 5) wherein $\tau_{upper}$ is the run time parameter of the upper layer 2 and $\tau_{base}$ is the run time parameter of the base layer 2 of the two layer material 1. Subsequently, the respective layer thickness values $d_{upper}$ and $d_{base}$ of the layered material to be examined are calculated while using previous knowledge of the diffusivity values $\alpha_{upper}$ and $\alpha_{base}$ according to the known evaluation method (Theory and Practice of Infrared 5 Technology for Non-destructive Testing, Xavier P. V. Maldague, John Wiley & Sons, Inc., 2001, pages 527-536) as $$d=\sqrt{\alpha\tau}$$

These values are, thereafter, combined to an image which covers the complete area.

To summarize, the evaluation of a total layer structure of a layered material 1 can be achieved. The evaluation can be done by imaging which has high solution in time as well as in space and is scalable with respect to both parameters. Thereby, a calibration free and quantitative reconstruction of the thermal material parameters can be made flexibly, quickly and robustly under industrial conditions.

SECOND APPLICATION EXAMPLE

FIG. 6 shows the application of the method of the invention to the case where the sample is a substrate 10 having a defect 11 which is, in this case, a pore containing air as a rule. The substrate can be a metal substrate, a semiconductor substrate or a top surface of a construction component, like a metal piston having a high heat flow velocity. The substrate 10 is heated up by a heating source (not shown) in a pulsed manner, for example by a flash as indicated by the arrows H. If heated in this way, the pore 11 is an obstacle to the heat flow in the substrate starting from the surface 12 of the substrate and directed into the substrate (from top to bottom in FIG. 6).

The pore 11 is an obstacle to the heat flow because of the transition of the heat flow velocity from the substrate 10 to the pore 11. At the pore 11, the heat flow is directed upwards (as viewed in FIG. 6) again and creates a hot spot 13 the shape of which reflects the shape of the 11 pore added the effect of dissipation of the heat sideways in the substrate 10 as viewed in FIG. 6. The area 14 below the pore 11 (as viewed in FIG. 6) is in the "shadow" of the pore and, consequently heated up differently from the rest of the substrate.

An image of the hot spot 13 and the rest of the surface of the substrate is captured along the line of the arrow P by a camera 15. The camera 15 produces an image 16 where the hot spot 13 produced by the pore 11 is clearly visible.

Since the instance in time when the hot spot 13 is created by the heat flow reflected from the pore 11 depends on the distance between the upper border of the pore 11 from the surface 12 of the substrate 10, the image of the pore 11 appears in an image which is delayed with respect to the excitation flash by the runtime of the heat flow between the pore 11 and the surface 12. Therefore, in the case of various defects like the pore 11 in different depths of the substrate will appear in images at different time distances from the excitation flash. By evaluating the image sequences in the manor described above, one can not only verify the existence of the any pores in the substrate 10 but also the depths location of the respective defects by correlating the time delay of their respective images from the excitation flash. It is apparent from the above specification that the invention is not restricted to the application in the two cases which have been disclosed as examples. Rather, the method of the invention is applicable in all cases where the speed (frames per second) of the camera is insufficient to produce the image sequences required for locating the existence and/or the depths location of any heat flow velocity transitions, such as border surfaces between layers of different flow velocity characteristics in a layered structure or defects like holes, pores and cuts in a substrate or a work piece, for example a piston for a vehicle motor, on the basis of one single image sequence.

The invention claimed is:

1. A method for a non-destructive, non-contacting and image forming examination of a sample by means of the heat flow thermography method where the examination consists of evaluating an existence and/or depth distance values of any heat flow velocity transitions below a surface of the sample,
   wherein the sample is excited by heat pulses of at least one excitation source, and a thermal flow originating therefrom is captured by at least one infrared sensor in an image sequence of thermal images, and wherein the thermal images obtained from the image sequence are evaluated by means of a signal and image processing and depicting a thermal flow with a resolution in time and in space, the method comprising:
   exciting the sample at least twice independently from each other by means of the heat pulses from the excitation source where a second excitation and any succeeding excitation is delayed with respect to a preceding excitation by a time delay whereby the start of the captured sequence happens at another defined point of time within the time between two images within an image sequence;

detecting the respective total thermal flow processes generated by the at least two excitation processes of the sample by the infrared sensor in the independent image sequences containing the excitation as well as the thermal answer signal from the sample, combining all captured image sequences to a total image sequence in which all images are arranged in a sequence which is correct in time with respect to the point of time of the pulse like excitation, and extracting from the total image sequence an indication of the depth distance of a heat flow velocity transition from a surface of the sample, wherein a run time parameter is extracted related to pixels from the thermal flow procedures of the total image sequence, and from the run time parameter, a depth distance value of a heat flow velocity transition from a surface of the sample is calculated and combined with other depth distance values to form an image covering the surface area of the sample.

2. The method according to claim 1, wherein the indication of the depth distance of a heat flow velocity transition from a surface of the sample comprises the run time parameters related to the surface areas of the sample in a pixel related manner.

3. The method according to claim 1, wherein the total image sequence is corrected such that the pixel related intensity curves comprise a strictly monotones behavior in the areas to be evaluated.

4. The method according to claim 1, wherein any image sequence extends up the point of time when an equilibrium condition is reached with respect to the dissipation of the heat applied during the excitation of the sample.

5. The method according to claim 1, wherein a periodic excitation of the layered material is used wherein the starting point of the imaging of the respective independent image sequence is displaced with respect to the starting point of the periodic excitation to another defined point in time.

6. The method according to claim 1, wherein the delay of the independent image sequences is carried out in equal time portions.

7. The method according to claim 1, wherein the length of the equal portions in time of the delay of the independent image sequences is defined as the quotient of the time between two images within an image sequence divided by the number of the independently captured image sequences n.

8. The method according to claim 1, wherein the image intensity of each captured image sequence is corrected so that all captured image sequences have the same intensity offset.

9. The method according to claim 1, wherein one of the captured image sequence is used as a reference sequence for correcting the image intensity in the rest of the captured image sequences.

10. The method according to claim 1, wherein the first captured image sequence serves as a reference sequence for correcting the image intensity in the rest of the captured image sequences.

11. The method according to claim 1, wherein the sample comprises a structure of a layered material comprising a base layer and at least one layer additional layer, wherein the run time parameter for the base layer and the run time parameter for the additional layer are extracted related to pixels from the respective thermal flow procedures of the total image sequence, and from the run time parameters respective depth distance values of a heat flow velocity transition from a surface of the layered structure are calculated which are put together to an image covering the surface area of the layered structure of the sample.

12. The method according to claim 11, wherein the reconstruction of at least one layer of the total layer structure of a layered material is carried out based on the physical model thereof wherein the run time parameters of the respective pixel related heat flow processes of the total image sequence are extracted by correlating the respective thermal answer signals of the layered material with the previously calculated pulse answer signals for different run times of appropriate lengths, and wherein all layer thickness values are calculated from the detected run time parameters in knowledge of diffusivity values of corresponding layers of the layered structure.

13. The method according to claim 1, wherein the sample comprises a substrate or a work piece including defects close to a surface of the substrate which defects are heat flow velocity transitions experienced by the heat flow from the surface of the sample into a body of the sample, wherein the indication of presence and depth distance of a particular defect is a hot spot in a respective image of the image sequence which respective image was taken at a time distance from the excitation of the sample related to the depth distance of the defect from the surface of the sample.

14. The method according to claim 1, wherein the run time parameter is extracted out of area of intensity curve of total image sequence.

15. The method according to claim 11, wherein the run time parameter of the base layer and the run time parameter of the additional layer are extracted out of respective areas of the intensity curves of total image sequence.

16. A method, comprising:

applying at least a first heat pulse and a second heat pulse to a sample;

with an infrared sensor, initiating capture of a first image sequence and a second image sequence responsive to the first heat pulse and the second heat pulse, respectively, wherein the first image sequence is initiated at a first time delay with respect to the first heat pulse and the second image sequence is initiated at a second time delay with respect to the second heat pulse; and based on the first image sequence, the second image sequence, the first time delay, and the second time delay, estimating a depth in the sample associated with heat flows responsive to the first heat pulse and the second heat pulse.

* * * * *